(12) United States Patent
Aneja

(10) Patent No.: US 6,232,486 B1
(45) Date of Patent: May 15, 2001

(54) MOLECULAR PROBES AND MODULATORS FOR PI-PLC AND PI 3-KINASE

(75) Inventor: Rajindra Aneja, Ithaca, NY (US)

(73) Assignee: Nutrimed Biotech, Ithaca, NY (US)

( * ) Notice: Subject to any disclaimer, the term of this patent is extended or adjusted under 35 U.S.C. 154(b) by 0 days.

(21) Appl. No.: 08/872,222

(22) Filed: Jun. 10, 1997

Related U.S. Application Data

(60) Provisional application No. 60/019,651, filed on Jun. 11, 1996.

(51) Int. Cl.$^7$ ..................................................... C07F 9/117
(52) U.S. Cl. .......................... 558/160; 558/161; 558/179; 558/180; 558/186
(58) Field of Search ..................................... 558/160, 161, 558/179, 180, 186

(56) References Cited

U.S. PATENT DOCUMENTS

| | | |
|---|---|---|
| 4,515,722 | 5/1985 | Yang et al. . |
| 5,053,399 | 10/1991 | Kozikowski . |
| 5,227,508 | 7/1993 | Kozikowski et al. . |

OTHER PUBLICATIONS

Elie, C.J.J. et al. Tetrahedron 45(11), 3477–3486 (1989).*
Lewis, K.A. et al. Biochemistry 32, 8836–8841 (1993).*
Chen, J. et al. Journal of Organic Chemistry 1996, 61(1), 393–397.*
Bruzik & Tsai, "Toward the Mechanism of Phosphoinositide–Specific Phospholipases C," *Bioorganic & Medicinal Chemistry*, vol. 2, No. 2, pp. 49–72, 1994.
Chen et al., Synthesis of Photoactivatable 1,2–0–Diacyl–sn–glycerol Derivatives of 1–L–Phosphatidyl–D–myo–inositol 4,5–Bisphosphate (PtdInsP$_2$) and 3,45–Trisphosphate (PtdInsP$_3$), *J. Org. Chem.*, vol. 61, pp. 6305–6312, 1996.

Gadella et al., "Enzymatic Synthesis of Pyrene–Labeled Polyphosphoinositides and Their Behavior in Organic Solvents and Phosphatidylcholine Bilayers," *Biochemistry*, vol. 29, pp. 3389–3395, 1990.

Gu & Prestwich, Synthesis of Phosphotriester Analogues of the Phosphoinositides PtdIns (4,5) P$_2$ and PtdIns (3,4,5) P$_3$, *J. Org. Chem.*, vol. 61, pp. 8642–8647, 1996.

Hendrickson et al., "Kinetics of *Bacillus cereus* Phosphatidylinositol–Specific Phospholipase C with Thiophosphate and Fluorescent Analogs of Phosphatidylinositol," *Biochemistry*, vol. 31, pp. 12169–12172, 1992.

Shashidhar et al., "A chromogenic substrate for phosphatidylinositol–specific phospholipase C: 4–nitrophenyl myo–inositol–1–phosphate," *Chem. Phys. Lipids*, vol. 60, pp. 101–110, 1991.

* cited by examiner

*Primary Examiner*—Michael G. Ambrose
(74) *Attorney, Agent, or Firm*—Williams, Morgan & Amerson

(57) ABSTRACT

This invention provides analogues of phosphatidylinositol-phosphates modified at one or more selected inositol-hydroxyls and optionally carrying reporter or anchoring groups attached in the lipid or the inositol residues, and, the synthetic intermediates and methods for the preparation of these analogues. The analogues are useful as research reagents in biomedical studies related to structure, function and therapeuticals, including reference materials for analyzing the metabolic products in safety and efficacy studies of 2- and/or 3-hydroxyl modified inositols and phosphatidylinositols as drug candidates.

3 Claims, 2 Drawing Sheets

Figure 1:
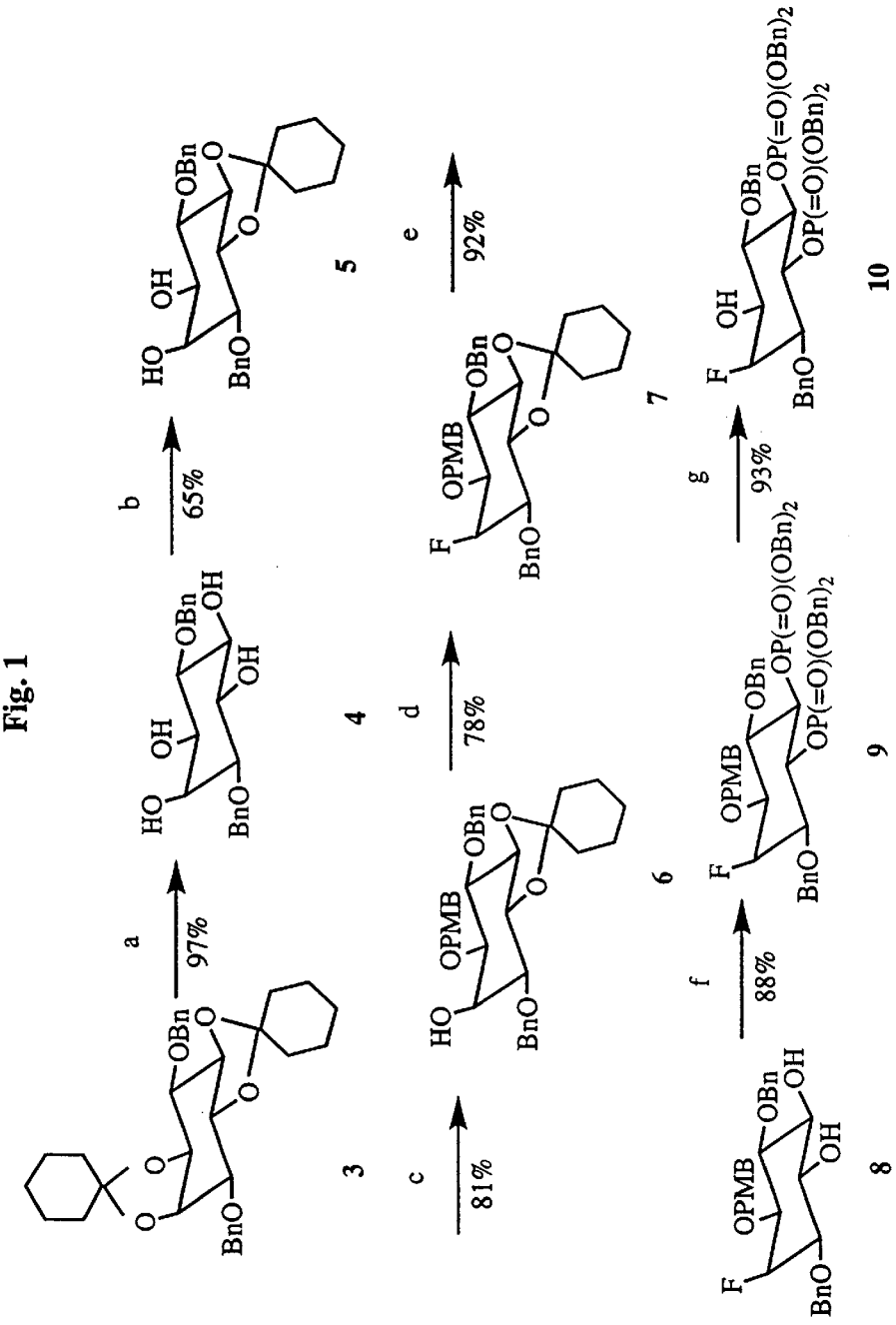

Scheme I: Synthesis of 1D-3,6-di-O-benzyl-2-deoxyfluoro-myo/scyllo-inositol-4,5-bis(dibenzylphosphate) 10. *Reagents and Conditions:* (a) HOAc/H$_2$O (90:10), 95 °C. (b) Cyclohexanone dimethylketal (1.2 eq.), DMSO, 40-45 °C, red. press. (c) Bu$_2$SnO, toluene, 110 °C, DMF, 4-MBnCl, CsF, 80 °C. (d) CH$_2$Cl$_2$, DAST, NEt$_3$, 35-40 °C. (e) Ethylene glycol (1.1 eq.), *p*-TSA, CH$_2$Cl$_2$, R.T. (f) (*i*-Pr)$_2$NP(OBn)$_2$, 1*H*-tetrazole, CH$_2$Cl$_2$, -40 °C, *m*-CPBA. (g) DDQ, CH$_2$Cl$_2$, R.T.

Scheme II: Synthesis of 1,2-di-O-hexanoyl-sn-glycero-3-phosphoric acid (15) and 1-O-hexanoyl-2-O-(ω-Cbz-aminobutanoyl)-sn-glycero-3-phosphoric acid (18). *Reagents and Conditions*: (a) NaOAc buffer pH 8.5, 37 °C, PLD. (b) Ether-NaOAc buffer pH 8.5, 37 °C, PLA$_2$. (c) ω-Cbz-aminobutanoic acid, DCC, DMAP, CHCl$_3$, R.T.

MOLECULAR PROBES AND MODULATORS FOR PI-PLC AND PI 3-KINASE

The present application claims priority to provisional application Ser. No. 60/019,651, filed Jun. 11, 1996.

This invention was partially made with funds provided by the Department of Health and Human Services under Grant No. NIH-GM51138. Accordingly, the United States Government has certain rights in this invention.

BACKGROUND OF THE INVENTION

This invention is concerned with certain structural and stereochemical analogues of the phosphoinositide group of cellular lipids, novel approaches for their preparation by synthesis and key starting materials and intermediates of these approaches. The phosphoinositides comprising 1D-1-(1',2'-di-O-fattyacyl-sn-glycero-3'-phospho)-myo-inositols or phosphatidylinositol (PtdIns) and its mono- and polyphosphate derivatives are key participants in the intracellular signaling cascade which is generated in response to stimulation of certain cell surface receptors by many agonists. Biosynthetic and metabolic transformations of the phosphoinositides are implicated in initiating, sustaining and regulating this signal cascade in an agonist and tissue specific manner. These lipid transformations are catalyzed by several families of enzymes including the phosphatidylinositol-specific phospholipase C (PI-PLC) and the phosphatidylinositol 3-kinase (PI 3-kinase). Stimulated hydrolysis of phosphatidylinositol-4,5-bisphosphate (PtdIns(4,5)$P_2$), the substrate preferred by the mammalian PI-PLC, is representative. This hydrolysis rapidly and simultaneously generates inositol-1,4,5-trisphosphate ($IP_3$) and sn-1,2-diacylglycerol (DAG). Both $IP_3$ and DAG are second messengers respectively inducing $Ca^{++}$ mobilization from intracellular stores and protein kinase C (PKC) activation and are implicated in many physiological responses including mitogenesis (Berridge, 1984; Nishizuka, 1983). Specific PI-PLC enzymes function also in releasing membrane-anchored proteins using glycosyl-PtdIns as the anchoring ligand. PI 3-kinase specifically associates with and is phosphorylated by activated growth factor receptors and oncoproteins which manifest protein-tyrosine kinase activity (Whitman et al, 1988; Auger et al, 1989). It phosphorylates PtdIns(4,5)$P_2$ specifically at the D-3 hydroxyl to produce phosphatidylinositol-3,4,5-trisphosphate (PtdIns(3,4,5)$P_3$) which is the putative novel and critical second messenger of growth signals (Auger et al, 1989; Carpenter and Cantley, 1990; Coughlin et al, 1989; Majerus, 1992). A complex role for PI 3-kinase and its products, the 3-phosphorylated phosphoinositides (3PPI), is emerging in the control of cell division and growth (Carpenter and Cantley, 1996). Additionally a role is seen for PI 3-kinase in transient actin polymerization and association between actin and cellular cytoskeletal elements, and a possible connection between this and the role in cell growth. Thus there is tremendous current interest in elucidating the structure, biochemical behavior, and physiological roles of the various isoforms of these key enzymes and in tracing the downstream targets of the products of their action on the phosphoinsoitides. Probes and modulators incorporating the core PtdIns(4,5)$_2$ structure as provided by the present invention are required for these multifarious ongoing research investigations.

Endogenous $IP_3$ is dephosphorylated and is reutilized with DAG for the resynthesis of PtdIns, the PtdIns is rephosphorylated to PtdIns-phosphates, and the latter are converted back to PtdIns by the action of PtdIns-phosphate phosphatases, in the overall PtdIns metabolic cycle. Exogenous inositols and PtdIns, including structurally modified analogues such as those disclosed in Kozikowski (U.S. Pat. No. 5,053,399), Kozikowski et al (U.S. Pat. No. 5,227,508), and, Yang et al (U.S. Pat. No. 4,515,722) are incorporated into the PtdIns cycle and ostensibly into the PtdIns-phosphate pool. The characterization of the biosynthetic PtdIns-phosphates produced from the aforementioned modified exogenous inositols and PtdIns derivatives requires the corresponding modified-PtdIns(4,5)$P_2$ and related derivatives as reference reagents. These reference reagents are provided by the present invention.

In the prior art (Yang et al, U.S. Pat. No. 4,515,722) synthesized 2-modified analogues of PtdIns and found these to be useful antiinflammatory/analgesic agents. These analogues all incorporated DL-inositol moieties and the preferred lipid moiety was 1-(3',4'-acyloxybutylphosphonyl. The same biological activity was also claimed for unspecified PtdIns-phosphate derivatives but no application as a research reagent was disclosed.

Several phosphoinositide analogues are known in the prior art relevant to the present invention. The fluorescent 1-pyrenebutyl myo-inositol-1-phosphate and the chromogenic 4-nitrophenyl myo-inositol-1-phosphate have been described as reagents for the assay of bacterial PI-PLC (Hendrickson et al, 1992; Shashidhar et al, 1991) but are poor substrates and considered to be inadequate reagents (Bruzik and Tsai, 1994). The preparation of a nanomolar quantity of a pyrene-labelled PtdIns(4,5)$P_2$ from the corresponding pyrene-labelled PtdIns by successive phosphorylations at 4-O and 5-O by partially purified PtdIns 4-kinase and PI 5-kinase has been reported also (Gadella et al, 1990) but the required enzyme reagents and method of preparation are not easily accessible. Synthetic PtdIns(4,5)$P_2$ labelled with photoactive p-benzoyldihydrocinnamoyl and related reporter groups covalently attached to either the 1'-acyloxy or the 1-phosphate have been reported recently (Gu and Prestwich, 1996; Chen et al, 1996). These analogues are broadly similar, but attachment of the reporter group at 1-phosphate creates a 1-phosphotriester analogue and thereby destroys the core 1-phosphodiester function which is an essential structural feature of PtdIns(4,5)$P_2$ and all phosphoinositide substrate of PI-PLC.

It is considered that a sufficient range of appropriate biochemical probes and modulators of these enzymes are not available (Bruzik and Tsai, 1994). Therefore, an objective of the present invention is to provide substrate analogues as structure/mechanism-based probes and modulators suitable for research studies on PI-PLC, PI 3-kinase and related enzyme families. Additional objectives are to provide novel approaches for their preparation by synthesis and key starting materials and intermediates of these approaches.

SUMMARY OF THE INVENTION

This invention comprises several synthetic analogues of the preferred phosphoinositide substrates of the mammalian PI-PLC and PI 3-kinase enzyme families, exemplified by PtdIns(4,5)$P_2$, which retain the core structural requirements for efficient bonding and catalysis, but in which the 2-OH is rendered non-nucleophilic by derivatization or replacement exemplified by 2-OAc and 2-deoxyfluoro respectively, and, which may additionally contain photoaffinity, fluorescent, spin, other reporter groups, and conjugands for linking to polymer, chromatographic matrix, or gold surfaces are incorporated in the fatty acyl or inositol residues as shown in structure. Thus, the invention provides substrate analogues as structure/mechanism-based probes and modulators suitable for research studies on PI-PLC, PI 3-kinase and related enzyme families. Additionally, it provides novel approaches for their preparation by synthesis, and key starting materials and intermediates of these approaches.

A BRIEF DESCRIPTION OF THE DRAWINGS

FIG. 1. Scheme I: Synthesis of 1D-3,6-di-O-benzyl-2-deoxyfluoro-myo-inositol-4,5-bis(dibenzylphosphate) 10

Figure 2:
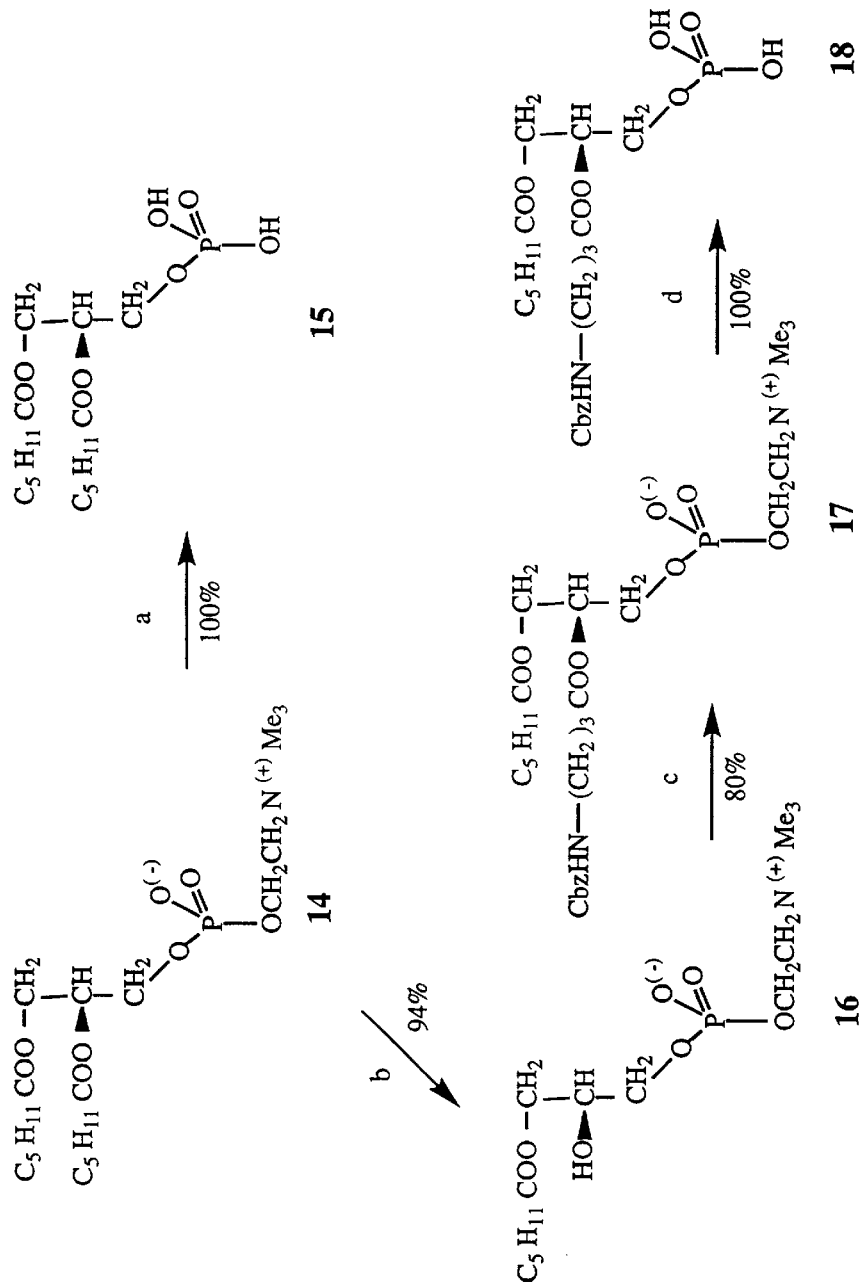

FIG. 2. Scheme II: Synthesis of 1,2-di-O-hexanoyl-sn-glycero-3-phosphoric acid (15) and 1-O-hexanoyl-2-O-(ω-Cbz-aminobutanoyl)-sn-glycero-3-phosphoric acid (18).

DETAILED DESCRIPTION OF THE INVENTION

Phosphatidyl-myo-inositol-4,5-bisphosphate (PtdIns(4,5)$P_2$) is a vital participant in intracellular signalling and allied processes, functioning as the preferred substrate of the mammalian phosphoinositide-specific phospholipase C (PI-PLC) and phosphoinositide 3-kinase (PI 3-kinase) enzymes, and, as allosteric activating factor of cellular regulatory proteins with and without pleckstrin homology domains.

In one embodiment, this invention comprises several synthetic analogues of PtdIns(4,5)$P_2$ (1, X=OH, $R^1$, $R^2$=Alkyl-C=O) incorporating one or more of the following modifying structural features: (i) the 2-OH is rendered non-nucleophilic by derivatization or replacement exemplified by 2-OAc and 2-deoxyfluoro respectively, and (ii) photoaffinity, fluorescent, spin, other reporter groups, and conjugands for linking to polymer, chromatographic matrix, or gold surfaces are incorporated in the fatty acyl or inositol residues as shown in structure 2.

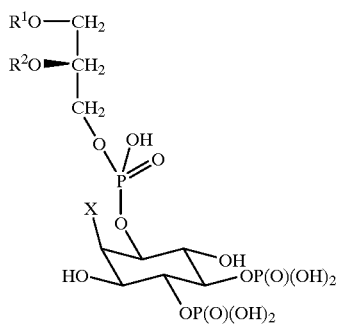

These analogues have utility as research reagents as structure- and mechanism-based competitive inhibitors of the mammalian PI-PLC, applicable inter alia as comparative probes of enzyme-action and protein-binding in PI-PLC, as novel substrate analogues of PI 3-kinase, and general probes of PtdIns(4,5)$P_2$-binding to cellular regulatory proteins. In the prior art, deoxyfluoro-inositols (Kozikowski et al, U.S. Pat. No. 5,053,399), and deoxyfluoro-phosphatidylinositols (Yang et al, U.S. Pat. No. 4,515,722; Kozikowski et al, U.S. Pat. No. 5,227,508) have been described. These are being developed as therapeutic agents and their metabolic products must be identified. The analogues disclosed in the present invention are likely metabolic products of the aforementioned prior art therapeuticals and therefore have utility as critical reference materials in analyses for establishing the presence or absence of such metabolic products. Several studies have provided information on the structural features of the substrate which are essential for PI-PLC enzyme activity. Most of the early findings were obtained with PI-PLC from bacterial sources although identical conclusions are emerging for the guinea pig uterus PI-PLC and the cloned isoforms. The consensus view has developed that the inositol-1-phosphate residue is required for substrate recognition as well as catalytic action. The presence of the free 2-OH is essential for catalytic action. Nucleophilic attack by this OH on the 1-phosphate phosphorus leads to the inositol-1:2cyclic-phosphates which are the diagnostic products of bacterial PI-PLC action (Lin et al, 1990; Volwerk et al, 1990). Binding to a lipid bilayer or equivalent lipid aggregate containing the substrate is essential for high activity. The crystal structure of the PI-PLC from Bacillus cereus in complex with its hydrolysis product, that is myo-inositol, has been solved to 2.6 Å (Heinz et al, 1995). This suggests that His32 acts as general base, accepting a proton from the myo-inositol 2-OH of PtdIns. Nucleophilic attack by the deprotonated 2-O on the phosphatidyl phosphorus results in a 5-cyclic phosphate and cleavage of DAG. Crystal structure of a mammalian PI-PLCδ1 deletion mutant in complex with its hydrolysis product, that is $IP_3$, has been determined (Essen et al, 1996; Grobler et al, 1996), and the complexes with Ins(1:2cyc)P and its 2-methylene analogue of have been studied (Essen et al, 1997). The data suggest a need and a mechanism for membrane attachment and for $Ca^{2+}$-dependent hydrolysis of PtdIns(4,5)$P_2$. In the proposed reaction mechanism, the 2-OH group is deprotonated in the first step by an internal general base, followed by nucleophilic attack on the 1-phospho group and release of DAG.

Another embodiment of this invention comprises two complementary strategies for syntheses illustrated for 2-deoxyfluoro and 2-OAc type analogues respectively. The approach for synthesis of the 2-deoxyfluoro PtdIns(4,5)$P_2$ (2, X=F) and analogues involves the preparation of (i) optically resolved O-protected myo-inositol-4,5-bisphosphate with a free 1-OH and (ii) 1,2-di-O-fattyacyl-sn-glycero-3-phosphoric acid (sn-3-phosphatidic acid), as inositol and lipid synthons respectively, (iii) coupling of the inositol 1-OH and the lipid phosphoric acid by phosphodiester condensation, and (iv) deprotection of the condensation product to obtain the target PtdIns(4,5)$P_2$ analogue. This approach is suitable for other analogues also including the 2-OAlkyl types. The 2-OCOR types illustrated by 2-OAc (2, X=OAc) are best prepared from a synthetic PtdIns(4,5)$P_2$ derivative in which the 3, 4, 5, and 6-OH or derived phosphates selectively carry temporary protecting groups and the unprotected 2-OH is rendered non-nucleophilic by derivatization to an ester or equivalent, followed by removal of the temporary protecting groups.

In yet another embodiment of this invention, the synthetic 2-modified analogues of PtdIns(4,5)$P_2$ and corresponding analogues lacking the 2-modification (2, X=OH) are offered as matched pairs.

Yet another embodiment of the invention comprises derivatives of PtdIns(4)P, and PtdIns(3)P series analogous to the PtdIns(4,5) series above.

The key inositol synthon for the 2-deoxyfluoro series was prepared from 1D-3,6-di-O-benzyl-1,2:4,5-dicyclohexylidene-myo-inositol 3 (Aneja et al, 1995) as outlined in Scheme I, FIG. 1. The two 2-deoxyfluoro epimers produced by the DAST reaction were separated by HPLC and the 2-epimer being the 2-deoxyfluoro-scyllo-inositol analogue was the major product.

The synthesis of 1,2-di-O-hexanoyl-sn-glycero-3-phosphoric acid (15) and 1-O-hexanoyl-2-O-(ω-Cbz-aminobutanoyl)-sn-glycero-3-phosphoric acid (18), outlined in Scheme II, FIG. 2, illustrates the general approach to sn-3-phosphatidic acids is adapted from literature methods (Aneja, 1974).

The inositol and lipid synthons were coupled using triisopropylbenzene-sulfonyl chloride in anhydrous pyridine at R. T (Aneja et al, 1997). The product was subjected to Pd—C catalyzed hydrogenolysis to remove the benzyl ether-ester protecting groups to obtain 2 (example, X=F, $R^1$=$R^2$=$C_{15}H_{31}CO$).

The structure of the inositol synthon 10 may be varied by replacing reaction of 6 with DAST in Scheme I step d by other reagents to produce 2-deoxy, oxo, O-acyl, O-alkyl, deoxyhalo or deoxydihalo analogues of die inositol synthon 10. Benzylation of 6 yielded the 2-O-benzyl analogue 11 of 7. Subsequent transformations exactly as in Scheme I gave 1D-2,3,6-tri-O-benzyl-myo-inositol-4,5-bis (dibenzylphosphate) 12, the key inositol synthon for PtdIns $(4,5)P_2$ unmodified in the inositol residue.

With 18 as the sn-3-phosphatidic acid, the products of condensation-hydrogenolysis yielded 1-O-hexanoyl-2-O-(amninobutanoyl)-sn-3-phosphatidyl-based PtdIns$(4,5)P_2$s; reaction of the primary amino group in these with "activated" reporter ligands gave the labelled analogues; for example reaction with N-hydroxysuccinimidyl-4-azidosalicylic acid gave the 4-azidosalicyl photoaffinity-labelled analogue.

In the second strategy for synthesis, 1D-(1,2-dihexadecanoyl-sn-glycero-3-phospho)-myo-inositol-3,6-di-O-benzyl-4,5-bis(dibenzylphosphate) was prepared by the method reported for the dihexanoyl derivative (Toker et al. 1994). On treatment with an OH acylating reagent, for instance $AC_2O$-DCC-DMAP, it gave the 2-O-acetyl derivative, which was hydrogenolyzed to the 2-OAc analogue of PtdIns$(4,5)P_2$ (2, X=OAc, $R^1$=$R^2$=$C_{15}H_{31}CO$). The short-chain acyloxy derivatives are prone to non-specific chemical hydrolysis.

The strategies for synthesis may be adapted for analogues incorporating reporter groups linked to the inositol residue in PtdIns$(4,5)P_2$s, for instance, by employing the 6-O-di-N-bezylaminoalkyl analogue of 3 as the starting material.

The utility of the key intermediates is reflected in the synthesis of the target PtdIns-phosphate analogues. The condensation products of the sn-3-phosphatidic acids and the optically resolved O-protected myo-inositol-4,5-bisphosphate with an additional free hydroxyl are particularly useful for incorporating other types of labels, such as radioactive or stable isotope based groups.

The action of PI-PLC on PtdIns$(4,5)P_2$ produces $IP_3$ and DAG. Ostensibly this involves intramolecular nucleophilic attack on the 1-phosphodiester by the 2-OH (Essen et al, 1996). The 2-modified analogues of PtdIns$(4,5)P_2$ of the present invention preclude the intramolecular nucleophilic action. As the core PtdIns(4,5 )P2 structure is retained, efficient interaction with the catalytic and allosteric binding sites results. Additional design and performance features may be incorporated for special applications, as in 1D-1-(1,2-di-O-n-butyl-sn-glycero-3-phospho)-2-deoxyfluoro-scyllo-inositol-4,5-bisphosphate prepared as a water-soluble analogue, stable to non-specific chemical hydrolysis, and useful for the preparation of co-crystallizates with PI-PLC isozymes for X-ray crystal structure analysis.

For use as analytical research reagents, the behavior of the 2-modified PtdIns$(4,5)P_2$ analogues in analytical chromatography was established. Thin layer chromatography is carried out preferably on silicagel layers with organic binder and impregnated with potassium oxalate and EDTA as scavengers for adventitious silica. These thin layer plates can be prepared from commercial TLC plates, preferably Cat. No. 47031, Uniplate from Analtech Inc., Newark, N.J. by dipping briefly in a solution of $K^+$ oxalate (1%) and $Na_4$ EDTA (0.6%) in methanol-water (3:2) followed by air-drying for 24 Hr. The plates are spotted with the analogue (1 to 10 μg) in solvent ($CHCl_3$—$CH_3OH$—$H_2O$, 2:1:0.2), development with eluant $CHCl_3$—$CH_3OH$—28% $NH_4OH$—$H_2O$ (2:2:1:1) at room temperature, and, visualization with $I_2$ vapor or other appropriate reagent. The Rf of unmodified PtdIns$(4,5)P_2$ is ca. 0.5, for analogues with w-aminoalkyl residues the Rf is in the range 0.2 to 0.3, and the presence of 2-deoxyfluoro substituent raises the Rf by ca. 0.05 to 0.1 compared with the 2-OH series. The TLC conditions can be translated into protocols for liquid chromatography including high performance liquid chromatography (HPLC) by techniques which are well known to practitioners of chromatographic separation.

For co-crystallization with PI-PLC isozymes, the water soluble 2-deoxyfluoro dibutylether PtdIns$(4,5)P_2$ analogue may be added as a solution in buffer to the enzyme solution. Other protocols may be applied to suit individual experiments.

The invention has been delineated with reference to certain specific and preferred embodiments and methods. However, it is stated that many modifications and variations may be made while remaining within the scope and spirit of the invention.

All referenced patents and publications are incorporated herein by citation.

EXAMPLES

1D-3,6-Di-O-benzyl-myo-inositol 1D-3,6-di-O-benzyl-1,2:4,5-di-O-cyclohexylidene-myo-inositol (5.0 g, 0.0096 mol), prepared by a literature procedure (Aneja et al, Tetrahedron Asymmetry (1995) 6, 17-18) was dissolved in 60 ml HOAc-$H_2O$ (9:1) and heated at 95–100° C. for 1 hr. The solution was evaporated to dryness under reduced pressure and the residue co-evaporated with $H_2O$, $CHCl_3$ and $CH_3OH$ to dryness. The crude residue of virtually pure 1D-3,6-di-O-benzyl-myo-inositol was used without purification: $[\alpha]_{589}$+11.76° (c 1.9, $CHCl_3$—$CH_3OH$ 1:1). MALDI TDF MS m/z 361, $^1H$ NMR (300 MHz, $CDOD_3$) δ ppm 3.205 (d, 1H), 3.235 (d, 1H), 3.41 (d, 1H), 3.445 (d, 1H), 3.586–3.661 (q or dd) 3.71–3.90 (Ψt , J 9.7 and 9.7 Hz), 4.02–4.18 (Ψt, J 2.69 and 2.14 Hz), 4.62–4.75 (q, 4H), 7.14–7.62 (m 10 H).

1D-3,6-Di-O-benzyl-4,5-O-cyclohexylidene-myo-inositol

To a solution of 1D-3,6-di-O-benzyl-myo-inositol (4.1 g ,0.011 mol) and cyclohexanone dimethylketal 8 ml (0.05 mol) in dry DMSO (20 ml), p-toluene sulphonic acid monohydrate (pTSA) (35 mg) was added. The mixture was evacuated at 40–42° C. (red. pressure) for 5 hr. The solution was neutralized with saturated $NaHCO_3$ solution and left at 0–5° C. overnight. The products were extracted with ethyl acetate, organic layer was dried over $Na_2SO_4$ and solvent evaporated. Resulting glassy material was triturated with $CH_2Cl_2$ which dissolved the cyclohexylidene derivatives and the mixture was filtered to remove the insoluble starting material (1.1 g). TLC ($CH_2Cl_2$-ethyl acetate 1:1) of the solution showed 1D-3,6-di-O-benzyl-1,2:4,5-O-cyclohexylidene-myo-inositol ($R_f$=0.9), a major product ($R_f$=0.75), another product($R_f$=0.55) and trace of the starting material($R_f$=0.2). The $CH_2Cl_2$ soluble material chromatographed on Silicagel 60 Å in ethyl acetate-$CH_2Cl_2$ (1:4) gave the dicyclohexylidene derivative (0.1 50g) and then the 1D-3,6-di-O-benzyl-4,5-O-cyclohexylidene-myo-inositol (2.27 g, 65%). Further elution with the same solvent in ratio 1:2 gave lD-3,6-di-O-benzyl-1,2-O-cyclohexylidene-myo-inositol (Aneja et al, loc. cit.) (0.450 g, 13%). $[\alpha]_{589}$ –33.2°(c 1.3,CHCl$_3$); MALDI TDF MS m/z 462.54, calc. 463.22 (M+Na)$^+$, $^1$H NMR (300 MHz, CDCl$_3$) δ ppm 1.44–1.85 (br,10H), 2.66(m,2H), 3.38(t, J 9.66 and 9.67, 1H), 3.54–3.61(m, 2H), 3.81(t, J 8.6 and 9.7, 1H), 4.05(t, J 9.67 and 9.67, 1H), 4.21(Ψt, 1H), 4.72(d, 2H), 4.95(q, 2H), 7.26–7.44 (m, 10H).

1D-3,6-Di-O-benzyl-4,5-O-cyclohexylidene- 1-(p-methoxybenzyl)-myo/inositol

A mixture of 1D-3,6-di-O-benzyl-4,5-O-cyclohexylidene-myo-inositol (2.35 g,0.0053 mol), Bu$_2$SnO (1.33 g, 0.0053 mol) and toluene (70 ml) was stirred under reflux with a Dean-Stark apparatus for azeotropic removal of the water for 2 hrs and then evaporated to dryness under reduced pressure. To the residue was added DMF (40 ml), CsF (2.43 g, 0.016 mol) and 4-methoxybenzyl chloride (1.2 ml, 0.0088 mol) at 0–5° C. The reaction mixture was warmed and stirred at 40° C. for 2 hrs and 1 hr at 60° C. The solution was cooled to r.t. and diluted with 100 ml CH$_2$Cl$_2$, washed with water, dried over Na$_2$SO$_4$ and concentrated. The crude product was chromatographed on Silicagel 60Å using gradient elution with CH$_2$Cl$_2$-acetone (99:1 to 95:5) producing 1D-3,6-di-O-benzyl-4,5-O-cyclohexylidene-1-(-methoxybenzyl)-myo-inositol, 2.37 g (79%): $[\alpha]_{589}$ –12.03° (c 1.11, CHCl$_3$)HMRS FAB$^+$ m/z 583.52, calc. (M+Na)$^+$ 583.277, $^1$H NMR (300 MHz, CDCl$_3$) δ ppm 1.40–1.83 (br,10H), 2.64 (br,1H), 3.28–3.46 (m,2H), 3.48–3.63 (dd or q 1H), 3.75–3.89 (s,3H), 3.96 (Ψt, J 8.59 and 9.67, 1H), 4.05–4.27 (m 2H), 4.55–5.08 (m, 6H), 6.74–7.00 (m, 2H), 7.13–7.58 (m, 12H).

1D-3,6-Di-O-benzyl-2-deoxy-fluoro-4,5-O-cycloxylidene-1-O-(p-methoxybenzyl)-myo/scyllo-inositol To 1D-3,6-di-O-benzyl-4,5-O-cyclohexylidene-1-(p-methoxybenzyl)-myo-inositol (0.9857 g, 0.00176 mol) in 25 ml toluene under nitrogen atmosphere and at r.t. was added diethylaminosulphur trifluoride (0.35 ml, 0.0026 mol). The reaction mixture was stirred at r.t. for 1 hr and then the temperature was raised to 60° C. for 4 hr. After cooling down to r.t. 50 ml of sat. NaHCO$_3$ solution were added. The mixture was extracted with 3×50 ml ethyl acetate and the extract was washed with 2×30 ml sat. NaCl solution. The organic layer was dried over K$_2$CO$_3$, filtered and concentrated to a dark yellow syrup. Column chromatography on Silicagel 60Å using gradient elution with hexane-CH$_2$Cl$_2$-ethyl acetate (95:4:1 to 50:25:25) gave pure 1D-3,6-di-O-benzyl-2-deoxy-fluoro-4,5-O-cycloxylidene-1-O-(p-methoxybenzyl)-myo/scyllo-inositol; 0.5894 g (60%): $[\alpha]_{589}$ –20.46°(c 0.5,CHCl$_3$) MALDI TDF MS m/z 587.19; calc. (M+Na)$^+$586; $^1$H NMR (300 MHz, CDCl$_3$) δ ppm 1.2–1.9 (br, 10H), 3.4–3.6 (m, 2H), 3.6–3.7 (m, 1H), 3.7–3.8 (m, 1H), 3.8 (s, 3H), 4.47–4.57 (t, J 8.6 and 8.05, 1H), 4.6–5.00 (m, 6.8–7.00 (m,2H), 7.15–7.51 (m, 12H).

1D-3,6-Di-O-benzyl-2-deoxy-fluoro-1-O-(p-methoxybenzyl)myo/scyllo-inositol

To a solution of 1D-3,6-di-O-benzyl-2-deoxy-fluoro-4,5-O-cycloxylidene-1-O-(p-methoxybenzyl)-myo/scyllo-inositol (0.566 g ,1.007 mmol) and ethylene glycol (0.11 ml, 1.9 mmol) in 6 ml CH$_2$Cl$_2$-hexane (2:1), 12 mg of p-toluenesulphonic acid monohydrate was added. Reaction mixture was stirred at r.t. for 1 hr, then neutralized with 15 μl triethyl amine and 1 ml sat. NaHCO$_3$ solution. The product was extracted with 3×5 ml CH$_2$Cl$_2$. Organic layer was dried over Na$_2$SO$_4$ and concentrated. Chromatography on Silicagel 60Å using CHCl$_3$ as eluent gave pure 1D-3,6-di-O-benzyl-2-deoxy-fluoro-1-O-(p-methoxybenzyl)-myo/scyllo-inositol 449.4 mg (92.6%). $[\alpha]_{589}$ +9.0° (c 1.0, CHCl$_3$) MALDI TDF MS $^1$H NMR (300 MHz, CDCl$_3$) δ ppm 2.6 (d, 2H), 3.35 (t, 2H), 3.45 (m, 2H), 3.65 (m, 1H), 3.83 (s, 3H), .4.4–4.6 (Ψt, J 2.7 and 6.44, 1H), 4.62–4.85 (m, 4H) 4.87–5.00 (dd, 2H), 6.75–7.00 (d, 2H), 7.18–7.60 (m, 12H).

1D-3,6-Di-O-benzyl-2-deoxy-fluoro-1-O-(p-methoxybenzyl)-myo/scyllo-inositol 4,5-bis-O-dibenzylphosphate To a mixture of 1D-3,6-di-O-benzyl-2-deoxy-fluoro-1-O-(p-methoxybenzyl)-myo-inositol (375 mg, 0.78 mmol) and 1H-tetrazole (358 mg, 5.11 mmol) in 5 ml dry CH$_2$Cl$_2$ was added N,N-diisopropyl dibenzyl phosphoramidite (0.87 ml, 2.6 mmol). The reaction mixture was stirred at r.t. for 10 min. The TLC in CHCl$_3$-diethyl ether (80:20) showed no starting material left (R$_f$=0.175). The mixture was cooled down to –50° C. (CHCl$_3$/liq.N$_2$) and 3-chloroperoxybenzoic acid (60–80% purity, 877 mg, 3.0 mmol) in 10 ml dry CH$_2$Cl$_2$ was added. The resulting solution was stirred at 0° C. for 15 min. The reaction mixture was diluted with 50 ml CH$_2$Cl$_2$ , 100 ml 20% Na$_2$SO$_3$ solution was added and stirred at r.t. for 1 hr (until a negative NaI reaction for peroxides is shown). Organic layer was washed with 3×50 ml sat. NaHCO$_3$ solution; 2×20 ml water and 2×25 ml sat. NaCl solution. Combined organic extracts were dried over Na$_2$SO$_4$, filtered and solvent evaporated. Crude reaction product was chromatographed on Silicagel 60Å eluting with a gradient of CHCl$_3$/diethyl ether (99:1 to 95:5) giving pure 1D-3,6-di-O-benzyl-2-deoxy-fluoro-1-O-(p-methoxybenzyl)-myo/scyllo-inositol 4,5-bis-O-dibenzylphosphate: 702.5 mg (90.1%). $[\alpha]_{589}$ –15.03° (c 0.9, CHCl$_3$) MALDI TDF MS m/z $^1$H NMR (300 MHz, CDCl$_3$) δ ppm 1.02–1.34 (dd, 5H), 2.04–2.3 (s, 1H), 3.38–3.9 {m,s, 8H [3.35 (t, 2H)], 3.45 (m, 2H), 3.65 (m, 1H), 3.8 (s, 3H)}, 4.4–4.6 (m, 1H), 4.7–5.3 (m, 14H), 6.6–6.9 (m, 2H), 7.0–7.5 (m, 32H).

1D-3,6-di-O-benzyl-2-deoxy-fluoro-myo/scyllo-inositol 4,5-bis-O-dibenzylphosphate To a 0° C. solution of 1D-3,6-di-O-benzyl-2-deoxy-fluoro-1-O-(p-methoxybenzyl)-myo/scyllo-inositol 4,5-bis-O-dibenzylphosphate (600 mg, 0.5986 mmol) in 6 ml CH$_2$Cl$_2$-H$_2$O (20:1) was added solid 2,3-dichloro-5,6-dicyano-1,4-benzoquinone (DDQ) (540 mg, 2.36 mmol). After 2 hr. the reaction mixture was diluted with cold sat. NaHCO$_3$ solution (200 ml) and extracted with CH$_2$Cl$_2$ (4×50 ml). The combined organic extracts were washed with brine, dried over Na$_2$SO$_4$, evaporated and the residue purified by column chromatography on Silicagel 60Å with gradient elution with CHCl$_3$-diethyl ether to give 1D-3,6-di-O-benzyl-2-deoxy-fluoro-myo/scyllo-inositol 4,5-bis-O-dibenzylphosphate: 387.2 mg (73.3%). $[\alpha]_{589}$ –12.2° (c 0.98, CHCl$_3$) MALDI TDF MS m/z 906.0, calc. (M+Na)$^+$ 905.85. $^1$H-NMR (300 MHz, CDCl$_3$) δ ppm 1.2 (s, 2H), 1.56 (s, 6H), 2.78 (s, ½H), 3.38 (Ψt, J 1H), 3.35 (m, 1H), 3.77 (m,1H), 4.45–4.58 (m, 4H), 4.6–5.1 (m, 10H), 5.24 (s, 8H), 7.75 (m, 30H).

1D-3,6-di-O-benzyl-1-O-(1',2'-O-dibutyl-sn-glycero-3'-phospho)-2-deoxy-fluoro-myo/scyllo-inositol 4,5-bis-O-dibenzylphosphate To a solution of 1D-3,6-di-O-benzyl-2-deoxy-fluoro-myo/scyllo-inositol 4,5-bis-O-dibezylphosphate of 41.1 mg (0.0466 mmol) (dried excessively over $P_2O_5$) in dry pyridine was added triisopropyl-benzene sulphonyl chloride 100 mg (0.33 mmol). After stirring for 15 mins. at r.t. 1,2-dibutyl-sn-glycero-3-phosphate(phosphatidic acid) 34.1 mg (0.12 mmol) was added. After 10 hr. at r.t. reaction mixture was hydrolyzed by diluting with $CH_2Cl_2$—$H_2O$ (20:1) and leaving at r.t. overnight. After evaporating the solvents to dryness the residue was extracted with anhydrous diethyl ether, which gave the crude reaction product. Purification on Silicagel 60Å with gradient elution with $CHCl_3$-triethylamine and subsequent chromatography eluting with $CHCl_3$—$CH_3OH$—$NH_4OH$ gave the product: 11.5 mg, 21.5%. $[\alpha]_{589}$ +6.22° (c 0.94, $CHCl_3$) MALDI TDF MS m/z; $^1H$ NMR (300 MHz, $D_2O$ ) δ ppm 0.7–0.8 (br, 3H), 0.95–1.03 (m, 15H), 1.1–1.3 (br,3H), 1.35–1.5 (Ψt, 3H), 2.55 (s, 3H), 2.8–3.0 (d, 1H), 3.3–3.45 (m, 10 or 15H), 3.5–3.66 (m, 3H), 3.7–3.85 (m, 3H), 3.9–4.1 (br, 1H), 4.15–4.3 (br, 1H), 4.35–4.4 (br, 1H), 4.65 (s); 1H NMR (300 mhz, DMSO) δ ppm 0.8–0.9 (br, 2H), 1.0–1.1 (m, 5H), 1.12–1.18 (t, 3H), 1.2–1.35 (Ψt, 6H), 2.08 (s, 1H), 2.35 (s,), 2.4–2.6 (br,), 2.65 (s,), 2.9–3.2 (dd, 7H)4.35 (t, 1H), 6.9–7.26 (Ψt, 5H).

1D-3,6-Di-O-benzyl-2-deoxy-fluoro-1-O-(1', 2'-di-O-palmitoyl-sn-glycero-3'-O-phospho)-myo/scyllo-inositol 4,5-bis-O-dibenzylphosphate To a solution of 1D-3,6-di-O-benzyl-2-deoxy-fluoro-scyllo-inositol 4,5-bis-O-dibezylphosphate (20.8 mg, 0.0236 mmol) in 0.2 ml of dry pyridine was added triisopropylbenzene sulphonyl chloride (15 mg, 0.0472 mmol). After stirring for 10 mins at r.t., 1,2-dipalmitoyl-sn-3-glycerophosphate (Na salt, 16.5, mg, 0.0246 mmol) was added. After 10 hrs at r.t. reaction mixture was diluted with 2 ml ethanol-free $CHCl_3$ and stirring at r.t. for another 3–4hrs. Water (1 ml) was added and solvents were removed on a rotary evaporator. The dry residue was extracted with anhydrous diethyl ether (3×5 ml), filtered and the ether was evaporated. The crude product was chromatographed on silicagel 60Å eluting with a gradient of $CHCl_3$—MeOH—$NH_4OH$ (99:1:0.1 to 80:20:2) to afford pure 1D-3, 6-di-O-benzyl-2-deoxy-fluoro-1-O-(1', 2'-di-0-palmitoyl-sn-glycero-3'-O-phospho)-myo-inositol 4,5-bis-O-dibenzylphosphate: 10.2 mg, 28.6%. $[\alpha]_{589}$ +10.8° (c 0.5, $CHCl_3$) MALDI TDF MS m/z, $^1H$ NMR: δ ppm 0.6–1.0 (m,5H), 1.0–1.4 (s, 2H), 2.2 (br, 4H), 4.0 (br, 1H), 4.4–5.0 (br, 5H), 5.3 (s, 1H), 6.9–7.5 (m, 12H).

1D-2-deoxy-fluoro-1-O-(1',2'-di-O-palmitoyl-sn-glycero-3'-O-phospho)-myo/scyllo-inositol 4,5-bis-O-phosphate 1D-3,6-di-O-benzyl-2-deoxy-fluoro-1-O-(1',2'-di-O-palmitoyl-sn-glycero-3'-O-phospho)-myo/scyllo-inositol 4,5-bis-O-dibenzylphosphate (5.5 mg, 0.0036 mmol) in 2 ml ethanol and 0.5 ml $CHCl_3$ was hydrogenated for 6 hrs using 10 mg Pd-black and $H_2$ gas at 45 psi. After filtering the catalyst and evaporating the solvent, 1D-2-deoxy-fluoro-1-O-(1',2'-di-O-palmitoyl-sn-glycero-3'-O-phospho)-myo/scyllo-inositol 4,5-bis-O-phosphate (2.4 mg, 67.8%) was obtained. 1H NMR (300 MHz, DMSO-$d_6$) δ ppm: 0.8–0.9 (m, 10H), 1.0–1.1 ( m,16H), 1.15–1.4 (br, 60H), 1.5–1.6 (Ψ, t, 4H), 2.1–2.3 (d,t, 2H), 2.35 (Ψt, 1H), 2.45–2.55? 2.55–2.6 (t, 4H), 2.6–2.66 (t, 1H), 2.68–2.74 (m, 4H), 2.88 (s, 1H), 3.34–3.42 (m, 18H), 3.5 (d, 1H), 3.98–4.06 (m, 4H), 4.1–4.18 (t, 1H), 5.1 (s, 1H), 7.8 (m, 1H).

1D-2,3,6-Tri-O-benzyl-1-(p-methoxybenzyl)-myo-inositol 1D-3,6-Di-O-benzyl-4,5-O-cyclohexylidene-1-(p-methoxybenzyl)-myo-inositol (29 mg, 0.052 mmol) was treated with 1.5 ml DMF, 2 mg (0.05 mmol) NaH (60%, in oil) and 6µl (0.05 mmol) benzyl bromide at 0–5° C. TLC (hexane-ethyl acetate 70:30) showed reaction was over. Excess NaH was destroyed by adding $DH_2O$ at 0–5° C. DMF and water were evaporated. Residue was extracted, evaporated to dryness.

To the crude material, 100 µl $CH_2Cl_2$, 20 µl of p-toluenesulfonic acid solution (dissolved in ethylene glycol, 140 mg/4 ml) were added. Reaction was stirred at r.t. for several hours. TLC ($CHCl_3$—MeOH 95:5) showed conversion was finished. Two drops of triethylamine was added. Reaction was diluted, extracted, dried and concentrated. Column chromatography of the crude material eluted with a mixture of $CHCl_3$—MeOH gave pure 1D-2,3,6-tri-O-benzyl-1-(p-methoxybenzyl)-myo-inosito. 21 mg, 70% $[\alpha]_D$+10.79° (c 1.39, $CHCl_3$).

1D-2,3,6-Tri-O-benzyl-1-O-(p-methoxybenzyl)-myo-inositol 4,5-bis-O-dibenzylphosphate To a solution of 1D-2,3,6-tri-O-benzyl-1-O-(p-methoxybenzyl)-myo-inositol (26.7 mg, 0.0468 mmol) in 2 ml $CH_2Cl_2$ (dried over $P_2O_5$), 1H tetrazole (26.25 mg, 0.37 mmol) and N,N-diisopropyldibenzylphosphoramidite (26.25 mg ,0.37 mmol) were added. Solution was stirred at r.t. for 30 mins. 3-chloroperoxybenzoic acid (71.1 mg, 0.41 mmol) was added at –40° C. Reaction was stirred at 0–5° C. for 15 mins. TLC (hexane-ethyl acetate 60:40) showed reaction was over. 20 ml 20% $Na_2SO_3$ solution was added, reaction was stirred for ½ hour. NaI test was checked (negative). Reaction was then extracted with $CH_2Cl_2$, washed with saturated $NaHCO_3$ solution, followed by saturated NaCl solution. $CH_2Cl_2$ layer was dried and concentrated. Column chromatography of the crude material eluted with a gradient of hexane-$CH_2Cl_2$-ethyl acetate gave pure 1D-2,3,6-tri-O-benzyl-1-O-(p-methoxybenzyl)-myo-inositol 4,5-bis-O-dibenzylphosphate. 37 mg, 70% $[\alpha]_D$–9.37°(c 1.03, $CHCl_3$).

1D-2,3,6-Tri-O-benzyl-myo-inositol 4,5-bis-O-dibenzylphosphate

A mixture of 1D-2,3,6-tri-O-benzyl-1-O-p-methoxybenzyl)-myo-inositol 4,5-bis-O-dibenzylphosphate (30 mg, 0.026 mmol), 1.5 ml $CH_2Cl_2$, 1drop of $DH_2O$ and 2,3-dichloro-5,6-dicyano-1,4-benzoquinone (12.5 mg, 0.055 mmol) was stirred at r.t. for 15 mins. TLC (hexane-ethyl-acetate 50:50) showed reaction was complete. Solution was then extracted, washed with cold saturated $NaHCO_3$ solution, followed by cold saturated NaCl solution. $CH_2Cl_2$ layer was dried and concentrated. Column chromatography of the crude material eluted with a gradient of hexane-$CH_2Cl_2$-ethyl acetate gave pure 1D-2,3,6-Tri-O-benzyl-myo-inositol 4,5-bis-O-dibenzylphosphate. 22 mg, 85% $[\alpha]_D$=–11.01° (c 0.99, $CHCl_3$).

ω-Cbz-aminobutanoic acid

N-anrinobutanoic acid (5.06 g, 0.05 mol) was treated with benzyl chloroformate (7.8 ml 0.055 mol) and NaOH solution (2 g in 50 ml $DH_2O$) alternatingly at 0–5° C. in 1 hr. Mixture was stirred at r.t. for 48 hrs. Reaction was extracted with $CHCl_3$ 4×30 ml. Aqueous layer was acidified to PH≈2–3. An oil precipitated and quickly solidified. White solid was filtered out, washed with water several times and dried on a furnel. White precipitates was then dissolved in $CH_2Cl_2$, filtered, dried over $Na_2SO_4$, filtered one more time and evaporated to dryness. 8.98 g, 75%, m.p.: 63–65° C.

1-O-Hexanoyl-2-O-(ω-Cbz-aminobutanoyl)-sn-glycero-3-phosphocholine

Preparation of anhydride: dicyclohexylcarbodi-imide (1.6128 g, 7.82 mmol) was dissolved in 10 ml dry $CCl_4$;

ω-Cbz-aminobutanoic acid (3.384 g, 14.26 mmol) was dissolved in a mixture of CCl$_4$ (25 ml) and CH$_2$Cl$_2$ (20 ml). Dicyclohexylcarbodi-imide solution was pipetted to the ω-Cbz-aminobutanoi acid solution. Mixture was stirred at r.t. for 1 hr until white precipitate appeared and was filtered. Esterification: 1-O-hexanoyl-sn-glycero-3-phosphocholine (1.0114 g, 2.85 mmol) was dissolved in dry CHCl$_3$ (20 ml), dimithylaminopyridine (0.426 g, 2.85 mmol) was added, followed by the anhydride solution prepared earlier. The solution was stirred for a short while before adding dicyclohexylcarbodi-imide (0.654 g, 3.17 mmol) in CCl (5ml). Mixture was stirred at r.t. for 48 hrs. Reaction was then filtered, precipitates were washed with less than 1 ml CCl$_4$. Solvents were evaporated, resulting viscous colorless residue was purified by chromatography on silicagel eluted with CHCl$_3$—MeOH gave 1-O-hexanoyl-2-O-(ω-Cbz-aminobutanoyl)-sn-glycero-3-phosphocholine. 1.3 g, 80%.

1-O-Hexanoyl-2-O-(ω-Cbz-aminobutanoyl)-sn-glycero-3-phosphoric acid

1-O-hexanoyl-2-O-(ω-Cbz-aminobutanoyl)-sn-glycero-3-phosphocholine (0.8063 g, 1.4 mmol) in 15 ml acetate buffer (PH 5.6) was sonicated. 100 ml acetate buffer, phospholipase D (4 mg) and ethanol free ether were added. Mixture was stirred vigorously for 1.5 hrs at 37° C. and white precipitates formed. To the cold (0–5° C.) reaction, a cold solution of CHCl$_3$ (140 ml), MeOH (280 ml) and concentrated HCl (1.2 ml) was added. Reaction was mixed well and aqueous layer was extracted with cold CHCl$_3$ 7×50 ml. Combined organic layer was filtered and evaporated to dryness. 0.68 g, 100%.

1D-1-[1'-O-Hexanoyl-2'-O-(ω-Cbz-aminobutanoyl)-sn-glycero-3'-phospho]-3,6-di-O-benzyl-myo-inositol-4,5-bis-O-dibenzylphosphate To a solution of 1D-3,6-di-O-benzyl-myo-inositol-4,5-bis-O-dibezylphosphate (33.5 mg, 0.038 mmol) (dried excessively over P$_2$O$_5$) in dry pyridine was added triisopropyl-benzene sulphonyl chloride (34.7 mg, 0.114 mmol). After stirring for 15 mins. at r.t., 1-O-hexanoyl-2-O-(ω-Cbz-aminobutanoyl)-sn-glycero-3-phosphocholine (36.2 mg, 0.076 mmol) was added. After 10 hrs. at r.t. reaction mixture was hydrolyzed by diluting with CH$_2$Cl$_2$—H$_2$O (20:1) and leaving at r.t. overnight. After evaporating the solvents to dryness the residue was extracted with anhydrous diethyl ether, which gave the crude reaction product. Purification on Silicagel with gradient elution with CHCl$_3$-triethylamine and subsequent chromatography eluting with CHCl$_3$—CH$_3$OH—NH$_4$OH gave 1D-1-[1'-O-hexanoyl-2'-O-(ω-Cbz-aminobutanoyl)-sn-glycero-3'-phospho]-3,6-di-O-benzyl-myo-inositol-4,5-bis-O-dibenzylphosphate: 24.7 mg, 48%.

1D-1-[1'-O-Hexanoyl-2'-O-(ω-aminobutanoyl)-sn-glycero-3'-phospho]-myo-inositol-4,5-bis-O-phosphate 1D-1-[1'-O-hexanoyl-2'-O-(ω-Cbz-aminobutanoyl)-sn-glycero-3'-phospho]-3,6-di-O-benzyl-myo-inositol-4,5-bis-O-dibenzylphosphate (24.7 mg, 0.018 mmol) was hydrogenated and recovered and characterized as described for 1D-2-deoxy-fluoro-1-O-(1',2'-di-O-palmitoyl-sn-glycero-3'-O-phospho)-myo-inositol 4,5-bis-O-phosphate.

LITERATURE CITED

Aneja R. (1974) Biochem. Soc. Trans., 2, 38–41.
S. G. Aneja, A. Parra, C. Stoenescu, W. Xia and R. Aneja (1997) Tetrahedron Lett., 38, 803–806.
Auger K. R., Serunian L. A., Soltoff S. P., Libby P., Cantley L. C. (1989) Cell, 57, 167–175.
Berridge M. J. (1984) Biochem. J., 220, 345.
Bruzik K. S. and Tsai, M-D. (1994) Bioorg. Med. Chem. 2, 49–72.
Carpenter C. L. and Cantley, L. C. (1990) Biochemistry, 29, 11147–56.
Carpenter C. L. and Cantley, L. C. (1996) Biochim. Biophys. Acta, 1288, M11–M16.
Carpenter C. L. and Cantley, L. C. Current Opinion in Cell Biology 1996, 8, 153–158.
Chen J., Profit A. A. and Prestwich G. D. (1996) J. Org. Chem. 61, 6305–6312.
Coughlin S. R., Escobedo J. A., Williams, L. T. (1989) Science, 243, 1191–94.
Essen L-O, Perisic O., Cheung R., Katan M. and Williams, R. L. (1996) Nature, 380, 595–602.
Essen L-O, Perisic O., Katan M., Wu, Y., Roberts, M. F. and Williams, R. L. (1997) Biochemistry, 36, 1704–1718.
Gadella T. W. J., Moritz A., Westerman J., and Wirtz K. W. A. (1990) Biochemistry, 29, 3389–3395.
Grobler J. A. and Hurley J. H. (1996) Protein Science 5, 680–686.
Gu Q. M. and Prestwich G. D. (1996) J. Org. Chem. 61, 8642–8647.
Heinz D. W., Ryan M., Bullock T. L., Griffith O. H. (1995) The EMBO J. 14, 3855–3863.
Hendrickson H. S., Hendrickson E. K., Johnson J. L., Khan T. H., and Chial H. J. (1992) Biochemistry, 31, 12169–12172.
Kozikowski A. P, U.S. Pat. No. 5,053,399.
Kozikowski A. P., Faug A. H. and Powis G. (1993) U.S. Pat. No. 5,227,508.
Lin G., Bennett F., and Tsai M-D. (1990) Biochemistry, 29, 2747–2757.
Majerus P. W. (1992) Annu. Rev. Biochem., 61, 225–250.
Nishizuka Y. (1983) Trends in Biochem. Sc., 8, 13.
Serunian L. A., Haber M. T., Fukui T., Kim J. W., Rhee S. G., Lowenstein J. M., and Cantley, L. (1989) J. Biol. Chem., 264, 17809–17815.
Shashidhar M. S., Volwerk J. J., Griffith O. H., and Keana F. W., (1991) Chem. Phys. Lipids, 60, 101–110.
Volwork J. J., Shashidhar M. S., Kuppe A., and Griffith O. H. (1990) Biochemistry, 29, 8056–8060.
Whitman M., Downes C. P., Keeler M., Keller T., Cantley L. (1988) Nature, 332, 644–46.
Yang S. S., Beattie T. R., Durette P. L., Gallagher T. F. and Shen T-Y. (1985) U.S. Pat. No. 4,515,722).

What is claimed is:

1. A phosphoinsitide analogue based on phosphatidylinositolphosphate, wherein the 2-OH is rendered non-nucleophilic by derivatization or replacement or wherein a reporter group or conjugand is incorporated in the fatty acyl or inositol residue; wherein the core structure and absolute stereochemistry of the unmodified phosphatidylinositolphosphate is maintained in said phosphoinositide analogue; and wherein said phosphoinositide analogue has the structure:

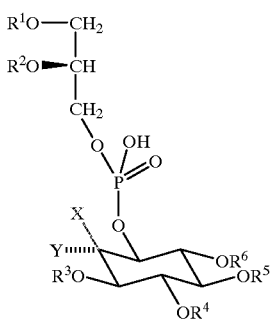

wherein at least one of $R^3$, $R^4$, $R^5$, $R^6$ is $P(=O)(OH)_2$, and wherein
(a) X=F, Cl, Br, OC(=O)R, OR, or OP(=O)(OH)$_2$, and Y=H; or X=Y=H; or
(b) X=H, and Y=F, Cl, Br, OC(=O)R, OR, or OP(=O)(OH)$_2$; or
(c) X=Y=F or (=O);
where R=alkyl, [especially methyl or ethyl,] alkenyl, alkynyl, ω-aminoalkyl, N-substituted-ω-aminoalkyl or N,N-disubstituted-ω-aminoalkyl; and wherein
(d) $R^1$=RC(=O) or R, $R^2$=R'C(=O) or R'
where R, R'=alkyl or alkenyl; and wherein
(e) $R^3$=H, or P(=O)(OH)$_2$
(f) $R^4$=H, or P(=O)(OH)$_2$
(g) $R^5$=H, or P(=O)(OH)$_2$
(h) $R^6$=H, P(=O)(OH)$_2$, ω-aminoalkyl, ω-aminoalkenyt, ω-sulthydrylalkyl, ω-carboxyalkyl, ω-(4-azidosalicyl amido)-alkyl, alkyl-aminotluorophor, alkyl-amidofluorophor, or alkyl-fluorophor.

2. A phosphoinositide analogue based on phosphatidylinositolphosphate, wherein the 2-OH is rendered non-nucleophilic by derivatization or replacement or wherein a reporter group or conjugand is incorporated in the fatty acyl or inositol residue; wherein the core structure and absolute stereochemistry of the unmodified phosphatidylinositolphosphate is maintained in said phosphoinositide analogue; and wherein said phosphoinositide analogue has the structure:

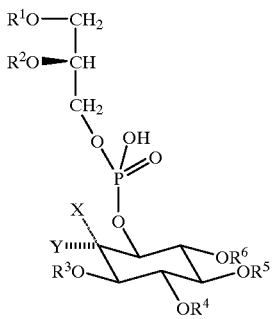

wherein at least one of $R^3$, $R^4$, $R^5$, $R^6$ is $P(=O)(OH)_2$, and wherein
(a) X=OH, and Y=H; and wherein
(b) $R^1$=RC(=O) or R, $R^2$=R'C(=O) or R'
where R, R'=ω-aminoalkyl, ω-(substitutedamino)-alkyl, ω(aminoalkenyl, ω-sulfhydrylalkyl, ωcaboxyalkyl, ω(4-azidosalicylarnido)-alkyl, ω-(substitutedamido)-alkyl, alkyl-aminofluorophor, alkyl-amidofluorophor, alkyl-fluorophor, hydroxylalkyl, or ketoalkyl; and wherein
(c) $R^3$=H, or P(=O)(OH)$_2$
(d) $R^4$=H, or P(=O)(OH)$_2$
(e) $R^5$=H, or P(=O)(OH)$_2$
(f) $R^6$=H, P(=O)(OH)$_2$, ω-aminoalkyl, ω-aminoalkenyl, ω-sulifthydrylalkyl, ω-carboxyalkyl, ω-(4-azidosalicyl amido)-alkyl, alkyl-aminofluorophor, alkyl-amidofluorophor, or alkyl-fluorophor.

3. A phosphoinositide analogue based on phosphaitdylinositolphosphate, wherein the 2-OH is rendered non-nucleophilic by derivatization or replacement and a reporter group or conjugand is incorporated in the fatty acyl or inositol residue; wherein the core structure and absoluie stereochemistry of the unmodified phosphatidylinositolphosphate is maintained in said phosphoinositide anaglogue; and wherein said phospihoinositide analogue has the structure:

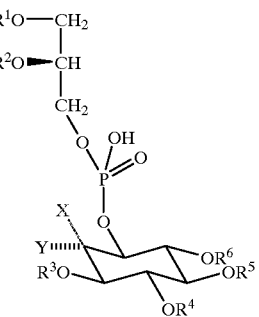

wherein at least one of $R^3$, $R^4$, $R^5$, $R^6$ is $P(=O)(OH)_2$, and wherein
(a) X=F, Cl, Br, OC(=O)R, OR, or OP(=O)(OH)$_2$, and Y=H; or X=Y=H; or
(b) X=H, and Y=F, Cl, Br, OC(=O)R, OR, or OP(=O)(OH)$_2$; or
(c) X=Y=F or (=O);
where R=alkyl, [especially methyl or ethyl,] alkenyl, alkynyl, ω-aminoalkyl, N-substituted-ω-aminoalkyl or N,N-disubstituted-ω-aminoalkyl; and wherein
(d) $R^1$=RC(=O) or R, $R^2$=R'C(=O) or R'
where R, R'=alkyl, alkenyl, alkynyl, ω-aminoalkyl, ω-(substirutedamino)-alkyl, ω-aminoalkenyl, ω-sulIfhydrylalkyl, ω-carboxyalkyl, ω-(4-azidosalicyl amido)-alkyl, ω-(substitutedamido)-alkyl, alkyl-aminofluorophor, alkyl-amidofluorophor, alkyl-fluorophor, hydroxylalkyl, or ketoalkyl; and wherein
(e) $R^3$=H, or P(=O)(OH)$_2$
(f) $R^4$=H, or P(=O)(OH)$_2$
(g) $R^5$=H, or P(=O)(OH)$_2$
(h) $R^6$=H, P(=O)(OH)$_2$, ω-aminoalkyl, ω-aminoalkenyl, ω-sulthydrylalkyl, ωcarboxyalkyl, ω-(4-azidosalicylamido)-alkyl, alkyl-aminofluorophor, alkyl-amidofluorophor, or alkyl-fluorophor.

* * * * *

UNITED STATES PATENT AND TRADEMARK OFFICE
CERTIFICATE OF CORRECTION

PATENT NO. : 6,232,486 B1
DATED : May 15, 2001
INVENTOR(S) : Aneja

It is certified that error appears in the above-identified patent and that said Letters Patent is hereby corrected as shown below:

Title page,
Last two lines, delete "3,45" and insert -- 3,4,5 -- therefor.

Column 3,
Line 9, please insert -- . -- at the end.
Line 47, after the structure depicted for structure 2, please insert the legend as follows:
-- 1. X=OH
   $R^1$, $R^2$=Alkyl-C=O
2. X=F, H, OAc, OAllyl,
   $OCH_2CH$=O, OMe, etc. or OH
   $R^1$, $R^2$=Alkyl-C=O,
   ($\omega$-$NH_2$)-Alkyl-C=O,
   Alkyl, Reporter Groups, etc. --.

Column 5,
Line 10, delete "die" and insert -- the -- therefor.
Line 18, delete "(amninobutanoyl)" and insert -- aminobutanoyl -- therefor.
Line 38, delete "bezylaminoalkyl" and insert -- benzylaminoalkyl -- therefor.

Column 7,
Line 13, delete "myo/inositol" and insert -- myo-inositol -- therefor.
Lines 27 and 28, delete "(-methoxybenzyl")" and insert -- (p-methoxybenzyl) -- therefor.
Line 62, delete "methoxybenzyl)myo/scyllo-inositol" and insert -- methoxybenzyl)-myo/scyllo-inositol -- therefor.

Column 8,
Line 17, delete "myo-inositol" and insert -- myo/scyllo-inositol -- therefor.

Column 9,
Line 27, delete "scyllo-inositol" and insert -- myo/scyllo-inositol -- therefor.
Line 41, delete "myo-inositol" and insert -- myo/scyllo-inositol -- therefor.

Column 10,
Line 14, delete "-myo-inosito" and insert -- myo-inositol -- therefor.
Line 53, delete "N-anrinobutanoic acid" and insert -- N-aminobutanoic acid -- therefor.
Line 60, delete "furnel" and insert -- funnel -- therefor.

Column 11,
Line 4, delete " aminobutanoi" and insert -- aminobutanoic -- therefor.
Line 8, delete "dimithylaminopyridine" and insert -- dimethylaminopyridine -- therefor.

UNITED STATES PATENT AND TRADEMARK OFFICE
CERTIFICATE OF CORRECTION

PATENT NO. : 6,232,486 B1
DATED : May 15, 2001
INVENTOR(S) : Aneja

It is certified that error appears in the above-identified patent and that said Letters Patent is hereby corrected as shown below:

<u>Column 11, cont'd,</u>
Line 11, delete "CCl" and insert -- CCl4 -- therefor.
Line 37, delete "bis-O-dibezylphosphate" and insert -- bis-O-dibenzylphosphate -- therefor.

<u>Column 13, claim 1,</u>
Line 32, delete "sulthydrylalkyl" and insert -- sulfhydrylalkyl -- therefor.
Line 33, delete "azidosalicyl amido" and insert -- azidosalicylamido -- therefor.
Line 34, delete "aminotluorophor" and insert -- aminofluorophor -- therefor.

<u>Column 13, claim 2,</u>
Line 66, delete "ωcarboxyalkyl" and insert -- ω-carboxyalkyl -- therefor.
Line 66, delete "azidosalicylarnido" and insert -- azidosalicylamido -- therefor.

<u>Column 14, claim 2,</u>
Line 9, delete "sulifthydrylalkyl" and insert -- sulfhydrylalkyl -- therefor.
Line 10, delete "azidosalicyl amido" and insert -- azidosalicylamido -- therefor.

<u>Column 14, claim 3,</u>
Line 15, delete "phosphaitdylinositolphosphate" and insert -- phosphatidylinositolphosphate -- therefor.
Line 19, delete "absoluie" and insert -- absolute -- therefor.
Line 21, delete "phospihoinositide" and insert -- phosphoinositide -- therefor.
Line 51, delete "substirutedamino" and insert -- substitutedamino -- therefor.
Line 52, delete "sullfhydrylalkyl" and insert -- sulfhydrylalkyl -- therefor.
Line 53, delete "azidosalicyl amido" and insert -- azidosalicylamido -- therefor.
Line 61, delete "sulthydrylalkyl" and insert -- sulfhydrylalkyl -- therefor.
Line 61, delete "ωcarboxyalkyl" and insert -- ω-carboxyalkyl -- therefor.

Signed and Sealed this

Ninth Day of April, 2002

*Attest:*

*Attesting Officer*

JAMES E. ROGAN
*Director of the United States Patent and Trademark Office*